United States Patent
MacLeod et al.

(10) Patent No.: US 8,897,526 B2
(45) Date of Patent: Nov. 25, 2014

(54) METHOD, SYSTEM, AND COMPUTER-READABLE MEDIUM FOR UNCOVERING AND PLANNING AN ACCURATE DENTAL PREPARATION

(75) Inventors: Roddy MacLeod, Charlotte, NC (US);
Daniel Michaeli, Riverdale, NY (US);
Volker Wedler, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 520 days.

(21) Appl. No.: 13/102,377

(22) Filed: May 6, 2011

(65) Prior Publication Data
US 2012/0282572 A1  Nov. 8, 2012

(51) Int. Cl.
*G06K 9/00* (2006.01)
*A61C 9/00* (2006.01)
*A61C 13/00* (2006.01)

(52) U.S. Cl.
CPC ............ *A61C 13/0004* (2013.01); *A61C 9/004* (2013.01)
USPC .......................................... 382/131; 382/128

(58) Field of Classification Search
USPC ................................................ 382/128, 131
See application file for complete search history.

(56) References Cited

U.S. PATENT DOCUMENTS

| 6,151,030 A | 11/2000 | DeLeeuw et al. |
| 6,319,006 B1 | 11/2001 | Scherer et al. |
| 7,796,811 B2 | 9/2010 | Orth et al. |
| 2004/0029068 A1* | 2/2004 | Sachdeva et al. ............... 433/24 |
| 2009/0220916 A1 | 9/2009 | Fisker et al. ............... 433/201.1 |
| 2011/0008751 A1* | 1/2011 | Pettersson .................... 433/167 |

FOREIGN PATENT DOCUMENTS

| WO | WO 2009/091438 A1 | 7/2009 |
| WO | 2009/140582 A2 | 11/2009 |

OTHER PUBLICATIONS

Sirona Dental Systems GmbH, "CEREC 3D, Operator's Manual, Software version 3.8X", Apr. 2011 (182 pages).
Saint Petersburg Company (Eltech-Med), Description of PARDUS-02 product, 2011 (2 pages) (avaialble at: http://www.eltech-med.com/english/index.php?page=pardus-02, last accessed May 31, 2012).
Sirona Dental Systems GmbH, GALILEOS Operating Instructions, Feb. 2008 (50 pages).
International Search Report and Written Opinion issued in connection with International Application No. PCT/EP2012/058329 on Sep. 6, 2012.

* cited by examiner

*Primary Examiner* — Tom Y Lu
(74) *Attorney, Agent, or Firm* — Fitzpatrick, Cella, Harper & Scinto

(57) ABSTRACT

A procedure for creating a dental prosthetic includes registering three-dimensional (3D) dental impression image data of a tooth restoration site and 3D x-ray image data of the tooth restoration site, and removing image data corresponding to soft tissue in the tooth restoration site from the 3D dental impression image data. A system for producing a dental prosthetic includes at least one processor operable to register 3D dental impression image data of a tooth restoration site and 3D x-ray image data of the tooth restoration site and remove image data corresponding to soft tissue in the tooth restoration site from the 3D dental impression image data.

20 Claims, 3 Drawing Sheets

METHOD, SYSTEM, AND COMPUTER-READABLE MEDIUM FOR UNCOVERING AND PLANNING AN ACCURATE DENTAL PREPARATION

BACKGROUND

1. Field

Example aspects described herein generally relate to dental restorations, and, in particular, to the use of CAD/CAM dentistry to produce a dental prosthetic.

2. Description of Related Art

Restoring or repairing one or more of a patient's teeth often involves the preparation and attachment of dental prosthetics such as crowns and bridges. Preparation of the dental prosthetic typically is preceded by preparing a tooth for the prosthetic, including removing any damaged, diseased, or decayed areas, removing (and/or resurfacing) hard tissue of the tooth into a shape suitable for a dental prosthetic, and preparing the preparation margin. The preparation margin is the portion of the tooth which will define the interface between the dental prosthetic and the unrestored surface of the hard tooth tissue. For example, when the dental prosthetic will be a crown, the preparation margin may be a ridge located at or near the gingival sulcus, the interface between the tooth and the surrounding gingiva.

Preparation of a dental prosthetic also is preceded by making an impression of the patient's jaw in the area of the restoration site, including the prepared teeth and the surrounding gingiva within the restoration site. In many instances, a physical impression is made. This provides an imprint of the restoration site, which often is made using an intraoral mold, and from which the dental prosthetic is produced. Alternatively, a digital impression can be made from three-dimensional (3D) image data of the restoration site, such as an optical impression taken with a visible-light camera. Because dental prosthetic manufacturing typically relies on a physical model of the restoration site, making a prosthetic from a digital impression requires a computer-aided design/computer-assisted manufacturing (CAD/CAM) system. Regardless of whether an impression is physical or digital, the impression should accurately reflect the physical features of a prepared tooth, particularly the preparation margin, and its surrounding gingiva. An accurate impression can yield a well-fitting dental prosthetic that is secure on the patient's tooth, and that is long-lasting and aesthetically pleasing. An ill-fitting dental prosthetic, on the other hand, can increase the patient's risk of infection or disease, and cause shifting in the prepared tooth and adjacent teeth.

Obtaining an accurate impression is not an insignificant task. A common way to obtain a physical impression of the dental site is to use a fluid mold material that can harden into a solid, such as polyvinyl siloxane (PVS). The mold material is used in combination with an impression tray to hold the fluid. The tray containing the fluid mold material is inserted into the patient's mouth and pressed onto the restoration site. The material then hardens intraorally, creating a permanent impression of the restoration site.

This procedure may be complicated, however, when the patient's soft gingival tissue obscures the preparation margin or otherwise interferes with the mold at or near the preparation margin. As a result of the obstruction, the mold material often cannot accurately record the preparation margin and, in turn, a dental prosthetic produced from the impression may not fit well onto the prepared tooth. Although increased pressure may be applied to the tray during mold hardening to displace the soft tissue, this often is not particularly effective, especially when the margin lies at or below the gingival margin.

There are several existing techniques for exposing the preparation margin when taking an impression. Some techniques rely on displacement of the soft gingival tissue. One example is "packing cord," a process in which one or more pieces of retraction cord are inserted into the gingival sulcus. The cord forces expansion of the gingival sulcus and displaces gum tissue away from the sulcus, thus creating physical separation between the gingival tissue surrounding the prepared tooth and the tooth itself. However, packing cord is a time consuming process. It also can cause significant pain to the patient and lead to irreversible damage of the gingiva. Another technique for displacing the gingival tissue is the use of a gingival retraction paste, such as Expasyl, a commercial paste manufactured by Kerr Corporation, which can be inserted into the gingival sulcus, where it creates a physical separation between the gingival tissue and the tooth. Because the paste must be removed prior to taking the impression, however, retraction of the gingival tissue is not permanent, and the tissue can rebound to its unretracted position and interfere with the impression. While some pastes include a hemostatic agent to assist with gingival separation after removal of the paste, this only increases the time of the temporary retraction.

Other techniques are directed to removing soft gingival tissue. For instance, electrosurgical devices or soft tissue lasers can be used to remove gingival tissue and expose the preparation margin. Removing gingival tissue, however, may not be adequate to sufficiently expose the margin. Also, tissue removal can be permanent, a consequence that may be adverse to the patient's oral health or cosmetically unappealing.

SUMMARY

In accordance with an example aspect herein, a procedure for creating a dental prosthetic includes registering 3D dental impression image data of a tooth restoration site and 3D x-ray image data of the tooth restoration site, and removing image data corresponding to soft tissue in the tooth restoration site from the 3D dental impression image data.

In accordance with another example aspect herein, a system for producing a dental prosthetic includes at least one processor operable to register 3D dental impression image data of a tooth restoration site and 3D x-ray image data of the tooth restoration site and remove image data corresponding to soft tissue in the tooth restoration site from the 3D dental impression image data.

In accordance with yet another example aspect herein, a computer-readable medium storing sequences of instructions is provided. The sequences of instructions include instructions which, when executed by a computer system, cause the computer system to register 3D dental impression image data of a tooth restoration site and 3D x-ray image data of the tooth restoration site, and remove image data corresponding to soft tissue in the tooth restoration site from the 3D dental impression image data.

In accordance with still another example aspect herein, a procedure for creating a dental prosthetic includes registering 3D dental impression image data of a tooth restoration site and 3D volume image data of the tooth restoration site, and removing image data corresponding to soft tissue in the tooth restoration site from the 3D dental impression image data.

Further features and advantages, as well as the structure and operation, of various example embodiments are described in detail below with reference to the accompanying drawings.

BRIEF DESCRIPTION OF THE DRAWINGS

The features and advantages of the example embodiments will become more apparent from the detailed description set forth below when taken in conjunction with the drawings.

DETAILED DESCRIPTION

Example aspects described herein relate to procedures, apparatuses, computer programs, and systems for creating a dental prosthetic using CAD/CAM dentistry. In an example embodiment, 3D dental impression image data and 3D x-ray image data of a tooth restoration site are generated. By registering the image data, dental structures imaged by the impression can be compared to dental structures imaged by the x-ray, and vice versa. Specifically, image data corresponding to soft tissue in the tooth restoration site can be removed from the 3D dental impression image data.

A tooth restoration site or restoration site generally is an area of a patient's oral cavity in which one or more teeth can be restored, repaired, or replaced by a dental prosthetic. A restoration site may (or may not) include areas in which a tooth is missing, such as when a patient has lost a tooth or a tooth has been removed during preparation for a dental impression. The tooth restoration site can include teeth adjacent to those that will be directly affected by a dental prosthetic, although it need not include such teeth. A tooth restoration site often includes the teeth (hard tissue) local to the site, as well as gingiva (soft tissue) surrounding the teeth, and sometimes also includes any other portion of the oral cavity local to the site, such as the alveolar bone. Because elective or cosmetic dental procedures may involve example embodiments described herein, it should be understood that a tooth restoration site need not include teeth receiving actual restoration or repair.

Dental prosthetics generally are, for example, artificial or man-made structures that replace part or all of a patient's dentition at a restoration site. Some examples of dental prosthetics include, without limitation, dental restorations—such as full and partial crowns, bridges, inlays, onlays, and veneers—dentures, and dental implants. A dental prosthetic can be permanent or temporary, and its use may be clinically indicated or elected by a patient.

A dental prosthetic that can form a tight seal to a prepared tooth can have good structural integrity and be long-lasting and cosmetically appealing. As discussed above, it can be difficult to produce and/or attach such a prosthetic when soft gingival tissue interferes with the preparation margin of the prepared tooth during the dental impression from which the prosthetic is made. Gingival tissue displacement or removal may not be an adequate way to remove or compensate for this interference. On the other hand, removing the interference of gingival tissue by manipulating 3D image data of the restoration site can improve the precision and quality of the dental prosthetic—both during production and attachment, and in the long term—and at the same time provide a comfortable experience for the patient.

Figure 2:
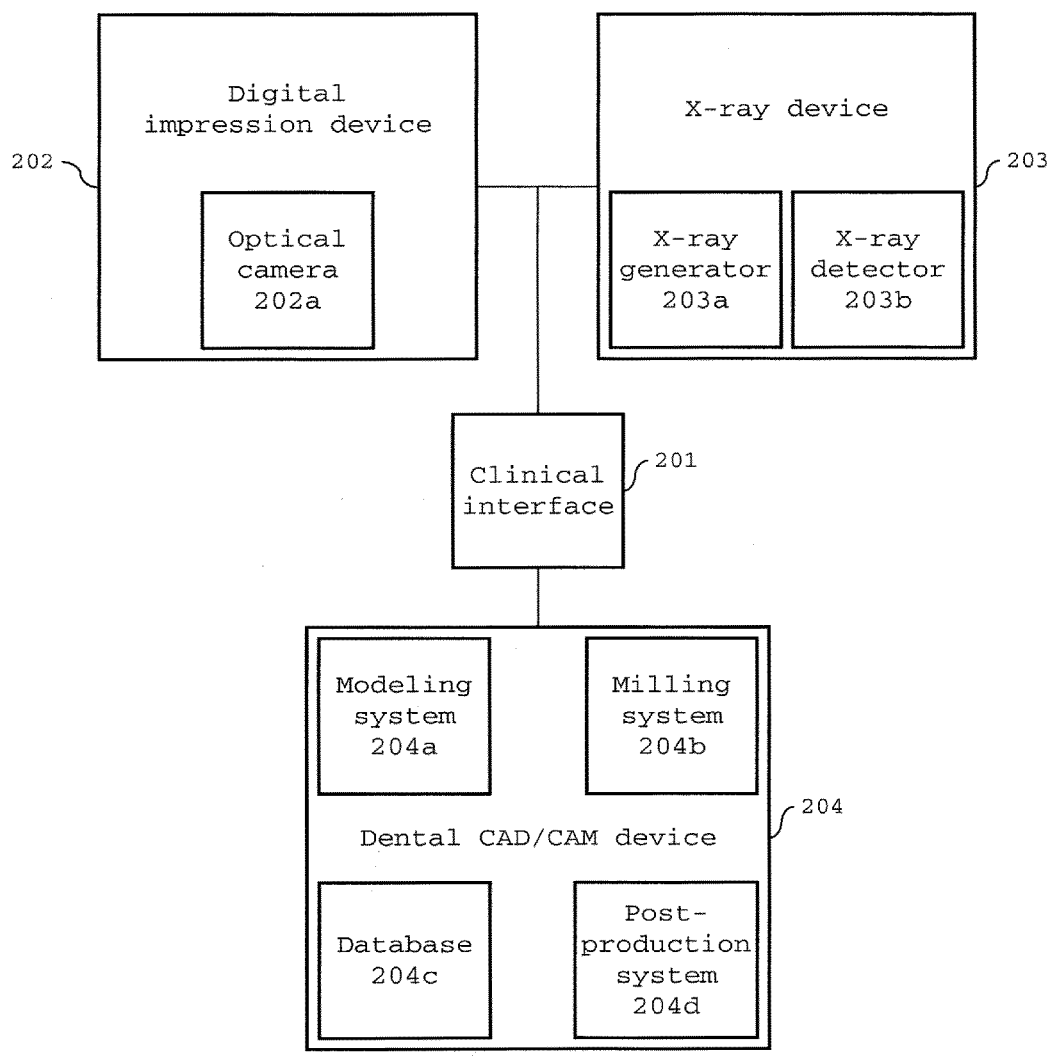
FIG. 2 is a diagram of a system configured in accordance with an example embodiment herein.

FIG. 2 is a diagram of a system configured in accordance with an example embodiment herein. Clinical interface 201 is connected to digital impression device 202, x-ray device 203, and dental CAD/CAM device 204. In one example, clinical interface 201 can be configured to control (or be controlled by) devices 202, 203, and 204. Clinical interface 201 also can be configured to send data to and receive data from devices 202, 203, and 204. Although FIG. 2 shows clinical interface 201 as a separate component from devices 202, 203, and 204, in other embodiments, clinical interface 201 may be included in, or otherwise form a part of, one or more of the devices 202, 203, and 204.

Clinical interface 201 may include, for example, a graphical user interface (GUI) or another type of user interface through which a user can interact with and/or control other devices connected to the clinical interface 201, input information, and/or be presented with outputted information. (Such capability, however, does not preclude a user from interacting with and/or controlling other devices directly, nor does it preclude any other device from having its own user interface.) In one example embodiment, clinical interface 201 has a capability for controlling the flow of data between other devices connected to the clinical interface 201.

In the system of FIG. 2, digital impression device 202 is arranged to obtain a 3D optical impression of a tooth restoration site. Digital impression device 202 includes, in one example, an optical digital camera 202a that acquires image data at visible wavelengths, such as a hand-held digital acquisition camera containing a blue light emitting diode (LED), or another type of image acquisition device. In various examples, optical digital camera 202a performs imaging procedures and generate image data intraorally (e.g., image acquisition occurring inside of a patient's mouth) and/or extraorally (e.g., image acquisition occurring outside of a patient's mouth). Also in various examples, optical digital camera 202a can perform image acquisition either automatically, e.g., without user intervention, or manually in response to operator commands. Additionally, in one example, optical digital camera 202a can automatically determine the depth of field and exposure time for acquired images.

X-ray device 203 is arranged to obtain a 3D diagnostic x-ray of a tooth restoration site. In one example, x-ray device 203 includes, for example, a 3D x-ray system including an x-ray generator 203a and an x-ray detector 203b, such as a charge-coupled device (CCD) that generates digital signals from incident light. The 3D x-ray system generates x-ray image data based thereon. The 3D x-ray system performs such procedures intraorally or extraorally. An example of an intraoral 3D x-ray system is the PARDUS-Stoma system manufactured by ELTECH-Med of Saint Petersburg, Russia. X-ray generator 203a and x-ray detector 203b can be independently and/or synchronously movable relative to a patient. In one example, the 3D x-ray system obtains image data by, for example, a computed tomography (CT) scan, in which 3D image data is generated from multiple 2D images, and can perform cone-beam tomography, although in other examples, other types of scans can be performed and other types of images can be obtained.

Although the illustrated embodiment shows devices 202 and 203 as separate components, in other example embodiments (not shown), digital impression device 202 and x-ray device 203 may be incorporated or combined into a single device or system. For example, the functionality of devices 203 and 204 can be performed by a single imaging device (e.g., a single housing containing components for acquiring a 3D optical impression and components for acquiring a 3D diagnostic x-ray), thereby permitting image data for a 3D optical impression and a 3D diagnostic x-ray to be generated by a single device.

Dental CAD/CAM device 204 is arranged to perform image processing procedures on image data. In example embodiments, dental CAD/CAM device is further arranged to produce a design of a dental prosthetic using a CAD procedure and/or produce a dental prosthetic using a CAM procedure.

In one example, dental CAD/CAM device 204 includes a modeling system 204a and a milling system 204b. Modeling system 204a performs image processing and CAD design procedures. Modeling system 204a includes design software that uses image data to design a CAD model of a dental prosthetic. In one example, the design software generates the CAD model without user input. In another example, the design software operates partly automatically and with some user input (e.g., manual marking of a particular surface such as a preparation margin). In an example embodiment, the modeling system has an associated database 204c of CAD models of teeth and/or dental restorations to facilitate design of a CAD model of a dental prosthetic.

Milling system 204b is configured to perform dental prosthetic production procedures. In an example embodiment, milling system 204b includes a milling machine having one or more computer-controlled burrs (not shown) or other grinding and/or cutting components to mill, cut and/or grind a material block into a pre-determined shape based on a CAD model, thereby producing a dental prosthetic.

In an example embodiment, dental CAD/CAM device 204 further includes a post-production system 204d for carrying out additional processing steps in producing a dental prosthetic, such as sintering procedures.

Components of the system illustrated in FIG. 2 can include software, hardware, or a combination thereof, and at least some of those components include (or are incorporated within) a computer system, one example of which is discussed below in connection with FIG. 3.

Figure 1:
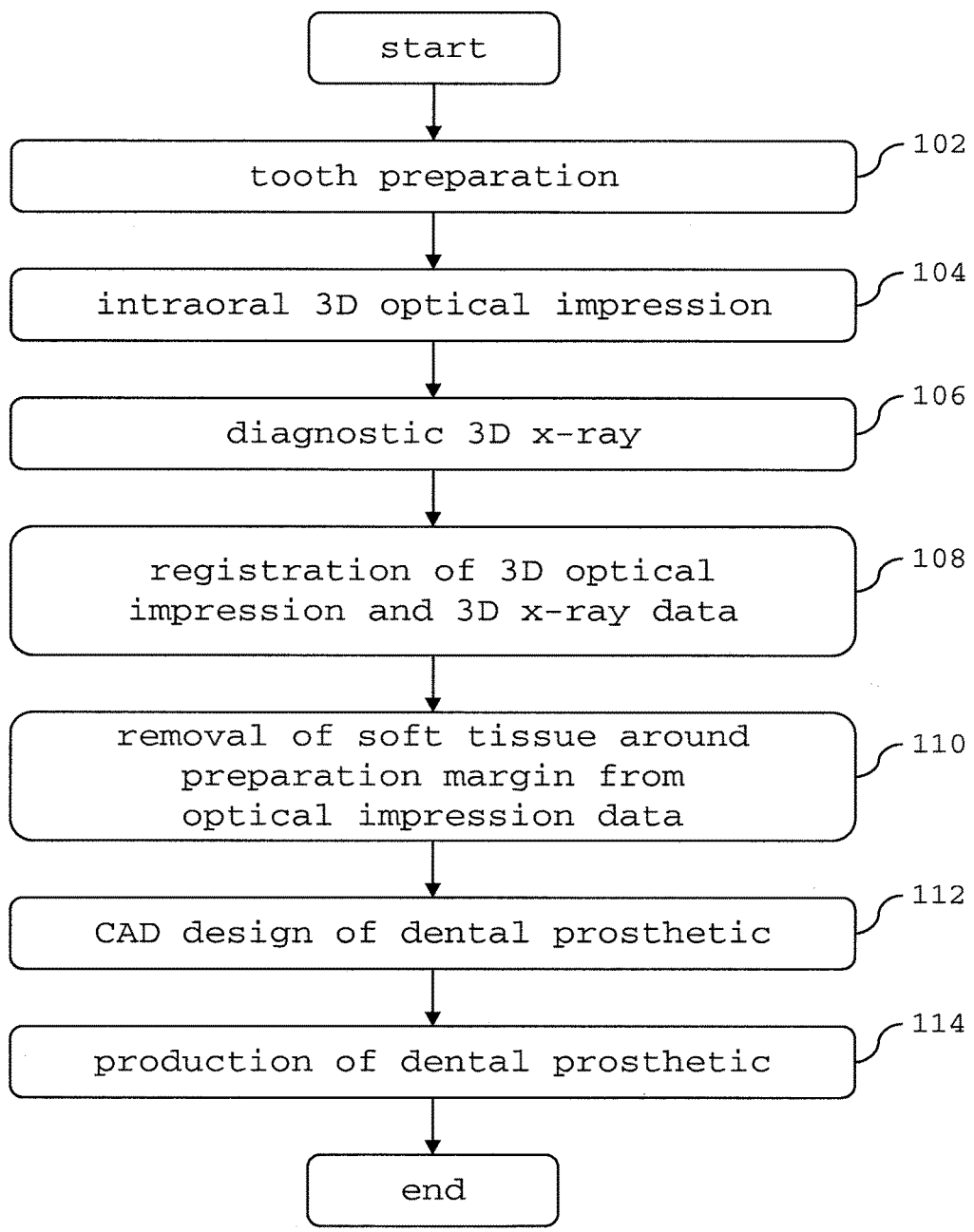
FIG. 1 is a flow diagram of an example procedure for creating a dental prosthetic, in accordance with an example embodiment herein.

FIG. 1 is a flow diagram of an example procedure for creating a dental prosthetic. Various steps of the procedure shown in FIG. 1 may be performed using one or more components of the system illustrated in FIG. 2. In an example embodiment, step 104 is performed using digital impression device 202, step 106 is performed using x-ray device 203, and steps 108, 110, and 112 are performed using dental CAD/CAM device 204.

At step 102, a tooth identified as suitable for (or otherwise affected by) a dental prosthetic is prepared for a digital impression. Procedures that can be performed at step 102 include, by way of example only (and without limitation), one or more of: cleaning the dental and gingival surfaces at the restoration site; removal of hard tooth tissue, including some or all of enamel of the tooth; and buildup of tooth structure, for example, by application of amalgam or resin. Step 102 also may involve preparation of multiple teeth and/or tooth sites, such as when the dental prosthetic is a bridge or denture, or when teeth adjacent to a restoration site must be reshaped, as deemed appropriate for the application of interest. Those of ordinary skill in the art will recognize that in certain circumstances, the tooth restoration site may require no preparation in order to successfully perform other steps for creating a custom dental prosthetic. Thus, at least some parts of step 102 may be optional.

At step 104, a 3D optical impression of the restoration site is taken. In an example embodiment, the 3D optical impression is taken at step 104 by, for example, digital impression device 202, which generates a recording of the visible surface features of the restoration site, including, for example, outer exposed surfaces of the teeth and gingiva. In one example, at least part of digital impression device 202 (e.g., optical digital camera 202a) is inserted into the patient's mouth so that the 3D optical impression can be acquired intraorally. In other examples, an extraoral technique for obtaining an image of the restoration site is employed. Also, in one non-limiting example, in acquiring image data, optical digital camera 202a conducts multiple scans of the restoration site in order to obtain a 3D optical impression of the entire restoration site.

The 3D optical impression obtained at step 104, however, may not be sufficient to produce an accurate dental prosthetic using CAD/CAM procedures. The interface of the soft gingival tissue and the hard tooth tissue occurs at the gingival sulcus, and typically a raised collar of gingival tissue—the marginal gingiva—surrounds the gingival sulcus. Thus, when a preparation margin of the prepared tooth lies near or below the normal location of the gingival sulcus, the gingiva near the prepared tooth can interfere with imaging of the preparation margin during the 3D optical impression. Accordingly, the inventors have discovered that another source of information on the preparation margin of the tooth can be useful to enable the dental prosthetic to be prepared, such as image data that accurately records the preparation margin.

At step 106, a 3D diagnostic x-ray image of the restoration site is obtained to record information on the anatomical structures in and underlying the restoration site. In one example, step 106 is performed to record interior features of the restoration site. For example, because the soft gingival tissue and the hard tooth tissue can differ in density and composition, x-ray images of the restoration site can show the contours of the tooth-gingiva interface at and below the gingival sulcus. X-ray images also may record the contours of the interface between the gingiva and the alveolar bone, as well as the interface between the enamel and cementum tissues of the tooth. Accordingly, the 3D diagnostic x-ray, which includes the soft gum tissue and hard tooth tissue, can be used to distinguish the position and extent of these two types of tissue.

3D x-ray images can contain (or be manipulated to contain) data on the volume of imaged structures. Accordingly, the 3D diagnostic x-ray image obtained at step 106 can include volume data on the soft gingival tissue and hard tooth tissue of the restoration site.

The ability to distinguish between soft and hard tissue within the oral cavity can enable image data of the soft gum tissue to be manipulated independently from the image data for the other hard tissue structures within the oral cavity. For example, x-ray image data for the soft gum tissue can be removed from various 3D images, as discussed below in connection with step 110.

In various example embodiments, the 3D diagnostic x-ray is obtained by x-ray device (system) 203. Depending on the configuration of the x-ray device 203, the patient may be seated or standing while the 3D diagnostic x-ray is taken. The x-ray device 203 can be configured to take multiple x-ray scans that include the restoration site. In one example, image data taken by the x-ray device 203 is obtained by computed tomography (CT) scans. Between scans, generator 203a and/or detector 203b are movable independently or synchronously relative to the patient. Depending on, for example, user preference or clinical observations, the diagnostic x-ray at step 106 can be obtained prior to the 3D optical impression at step 104 instead of afterwards as represented in FIG. 1. In other example embodiments, step 106 is performed simultaneously with step 104, or nearly so.

At step 108, image data from the 3D optical impression of step 104 and image data from the 3D diagnostic x-ray of step 106 are registered. Example procedures for registering optical and x-ray images are discussed in U.S. Pat. No. 6,319,006, issued Nov. 20, 2001, titled "Method for producing a drill assistance device for a tooth implant," which is hereby incorporated by reference herein in its entirety. In one non-limiting example, registration is a process by which two or more sets of image data are processed in order to obtain a reference system that is common to the sets of image data. Registration can include, in one example, the alignment of images. In one example, where various sets of image data have different imaging conditions (e.g., obtained by different imaging means, or obtained at different times), registration can be performed prior to, for example, combining the sets of image data, displaying a single coherent image containing data from multiple sets, or performing operations or calculations on data from one or more of the sets. Depending on the application of interest, registration may include combining, modifying, and/or altering one or more sets of image data, and may further include creating one or more new sets of image data from registered image data.

In an example embodiment, the image data is registered at step 108 by an automatic image processing procedure that incorporates one or more known registration algorithms. Registration of image data from the 3D optical impression and the 3D diagnostic x-ray yields image data that includes the surface features of the restoration site, as well as the anatomical structures in and underlying the restoration site. Such image data can be used, for example, to view x-ray-imaged and 3D impression-imaged features of the restoration site together, and/or to manipulate 3D impression image data relative to (or in conjunction with) x-ray image data.

At step 110, image data of the 3D impression that corresponds to soft gum tissue is removed from the 3D optical impression obtained in step 104. In an example embodiment, the image data corresponding to soft gum tissue is removed using an automated image processing procedure. Because the 3D optical impression is registered to the 3D diagnostic x-ray, which can accurately image the position and extent of the soft gum tissue and distinguish the soft gum tissue from the hard tissue in the oral cavity, the x-ray image data can be used to remove the soft gum tissue from the 3D optical impression in step 110. Specifically, the image data corresponding to soft gum tissue local to the preparation margin of a tooth can be removed from the 3D optical impression. Doing so can reveal or enhance the accuracy of the 3D impression's record of the preparation margins of the teeth at the restoration site. Removal of the soft gum tissue at step 110 can be performed automatically or manually (using, e.g., clinical interface 201), or by a combination thereof, such as by, for example, automatic removal accompanied by manual confirmation, adjustment, and/or alteration.

In one example, removal of the soft gum tissue from the 3D optical impression at step 110 can include adjusting one or more image data parameters (e.g., transparency, focus, and color). For example, the transparency of the soft gum tissue image data can be changed (e.g. from 100% opacity to 50% opacity or 0% opacity) at step 110. Example algorithms for changing transparency in images are discussed in U.S. Pat. No. 6,151,030, issued Nov. 21, 2000, titled "Method of creating transparent graphics," which is hereby incorporated by reference herein in its entirety. By adjusting parameters of the image data, the soft gum tissue can be deemphasized (or emphasized) from the x-ray image data on, for example, a display of the image data. Parameters may be adjusted automatically and/or manually, such as by manipulating a control on a user interface (e.g., a toggle that turns the transparency of soft gum tissue image data on and off, or a sliding scale for selecting a desired level of transparency for soft gum tissue image data) such as clinical interface 201. Where parameters of image data are adjusted at step 110, such adjustment by itself can constitute the removal of soft gum tissue.

Of course, it is not required that all soft gum tissue be removed from the 3D optical impression in step 110, and such removal may not be desired in some cases. Instead, in one example, removal of the soft gum tissue at step 110 may be limited to removal of only a predetermined amount of soft tissue, and/or only the soft tissue local to the preparation margin of one or more teeth.

At step 112, a dental prosthetic for the restoration site is designed. In an example embodiment, the dental prosthetic is designed using a CAD procedure. Although any suitable CAD procedure may be used, an example design procedure begins by demarcating the preparation margin of the prepared tooth on a 3D optical impression that has the soft gum tissue removed. Demarcation is a computer-assisted procedure by which the location of a preparation margin of a tooth is identified, for example, on image data and/or in a computer model. Any suitable demarcation procedure can be used. Based on the preparation margin, a particular prosthesis shape is selected from among multiple predetermined shapes stored, for example, in a database on a computer system, such as database 204c. The selected shape is then compared to the 3D optical impression to obtain an approximate design for the dental prosthetic. If deemed necessary, the approximate design is corrected, for example, by adjusting its shape or the portions where it will contact the prepared tooth. If no corrections are deemed necessary, the approximate design for the dental prosthetic is deemed complete. Design of a dental prosthetic at step 112 can be performed automatically or manually.

The dental prosthetic is produced at step 114. In an example embodiment, the dental prosthetic is produced by a CAM system, such as a milling machine or milling system 204b, using the CAD design generated at step 112. In other examples, the CAD design can be sent, transmitted (e.g., over a communication network), or otherwise provided to a dental laboratory or other prosthetic manufacturer, where a traditional dental prosthetic can then be produced based on the design (e.g., using a milling machine).

The dental prosthetic produced at step 114 can produced from any suitable material (or materials) including, but not limited to, a dental composite resin, a ceramic substance such as feldspar, porcelain, and zirconia, a metallic substance such as cobalt alloy and titanium, and/or combinations of two or more thereof.

As discussed above, the procedure of FIG. 1 includes the removal of soft gum tissue from a 3D optical impression by using 3D diagnostic x-ray data. Such x-ray data may include data obtained, for example, by CT, cone-beam CT, and/or tomosynthesis scans. However, in other example embodiments, soft gum tissue can be removed from a 3D optical impression using data obtained by another imaging technique that provides 3D volume image data, non-limiting examples of which include ultrasonography, magnetic resonance imaging (MRI), or positron emission tomography (PET). For example, there may be motivation to avoid or minimize the exposure of a patient to ionizing radiation. In such a case, for example, step 106, i.e., obtaining a 3D diagnostic x-ray, can be replaced by a step of obtaining a 3D diagnostic ultrasound or another type of image not involving ionizing radiation.

Where an imaging technique other than an x-ray technique is used in a procedure for creating a dental prosthetic, the procedure can be similar to the procedure illustrated in FIG. 1, except that the alternative imaging technique is used to obtain 3D diagnostic image data at step 106.

Figure 3:
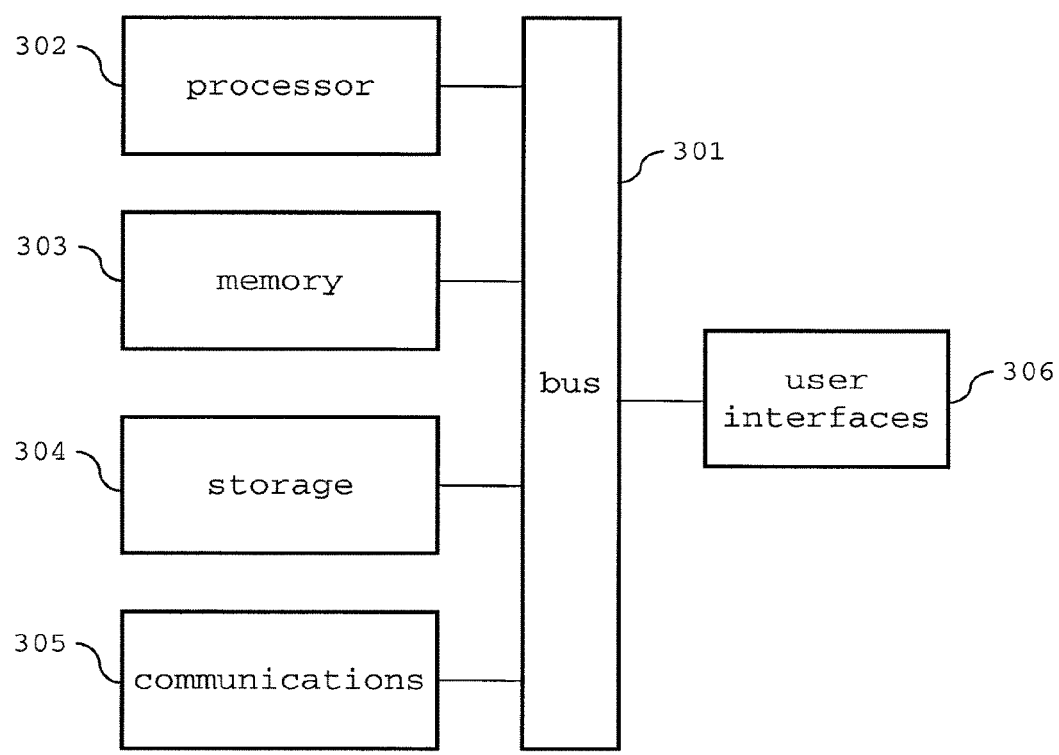
FIG. 3 is an architecture diagram of an example computer system or device which can be used in the practice of example embodiments herein.

FIG. 3 is a diagram of an example computer system. The system, in one example embodiment, may form at least part of one or more of the components illustrated in FIG. 2, and may be configured to perform one or more steps of the procedure illustrated in FIG. 1. The system of FIG. 3 includes a processor 302, a memory 303, a storage device 304, a communications device 305, and user interfaces 306, all of which are coupled to a bus 301.

Processor 302 can communicate with the other components of the computer system through bus 301. Storage device 304 includes one or more computer-readable media. Storage device 304 can be configured to read and write data including program instructions that may be executed by processor 302 and operating systems (e.g., a general-purpose operating system, such as Microsoft Windows and UNIX, or a custom operating system) that allow processor 302 to control the operation of the other components. Communications device 305 can be configured to allow processor 302 to communicate with, for example, a network and the internet. User interfaces 306 can include input devices (e.g., keyboards, mice, joysticks, trackpads, stylus tablets, microphones, and cameras), output devices (e.g., video displays, printers, and speakers), and input/output devices (e.g., touch screens). User interfaces 306 can form at least part of any of the devices, components, and/or systems discussed herein.

Processor 302 is configured to perform part (or all) of any of the procedures described herein, depending on which component(s) of FIG. 2 the computer system forms a part of. For example, the procedures can be stored on storage device 304 in the form of computer-readable program instructions. To execute a procedure, the processor loads the appropriate instructions, as stored on storage device 304, into memory 303, and then executes the loaded instructions.

In the foregoing description, example aspects of the invention are described with reference to several example embodiments. Accordingly, the specification should be regarded as illustrative, rather than restrictive. Similarly, the figures illustrated in the drawings, which highlight the functionality and advantages of the invention, are presented for example purposes only. The architecture of the present invention is sufficiently flexible and configurable, such that it may be utilized (and navigated) in ways other than those shown in the accompanying figures.

Software embodiments of example aspects of the invention may be provided as a sequence of instructions, or software, which may be stored on an article of manufacture, e.g., a computer-readable medium having instructions. The instructions on the computer-readable medium may be used to program a computer system or other electronic device. The computer-readable medium may include, but is not limited to, floppy diskettes, optical disks, CD-ROMs, and magneto-optical disks or other types of media suitable for storing electronic instructions.

The techniques described herein, when performed using a computer system, are not limited to any particular software configuration. They may find applicability in any computing or processing environment. The terms "computer-readable medium" and "memory" refer to any medium that is capable of storing, encoding, or transmitting a sequence of instructions for execution by a computer system and that causes the computer system to perform any technique described herein. Furthermore, it is common in the art to speak of software, in one form or another (e.g., program, procedure, process, application, logic, and so on) as taking an action or causing a result. Such expressions are merely a shorthand way of stating that the execution of the software by a computer system causes the processor to perform an action to produce a result. In other embodiments, functions performed by software can instead be performed by hardcoded modules, and thus the invention is not limited only for use with stored software programs. In addition, it is not necessary that procedures described herein be performed with a computer system, and instead they can be performed, in whole or in part, by a human operator.

Although example aspects of the invention have been described in certain specific embodiments, many additional modifications and variations would be apparent to those skilled in the art. It thus should be understood that this invention may be practiced in ways other than those specifically described. Thus, the present example embodiments, again, should be considered in all respects as illustrative and not restrictive.

What is claimed is:

1. A procedure for creating a dental prosthetic, the procedure comprising:
   registering three-dimensional (3D) dental impression image data of a tooth restoration site and 3D x-ray image data of the tooth restoration site;
   automatically removing image data corresponding to soft tissue in the tooth restoration site from the 3D dental impression image data based on a distinction in the 3D x-ray image data between soft tissue and hard tissue; and
   demarcating, in the 3D dental impression image data, a preparation margin of a prepared tooth from which soft tissue was removed, in the tooth restoration site.

2. A procedure according to claim 1, further comprising:
   generating the 3D dental impression image data; and
   generating the 3D x-ray image data.

3. A procedure according to claim 2, further comprising generating a model of a dental prosthetic based on the 3D dental impression image data in which the image data corresponding to soft tissue in the tooth restoration site has been removed.

4. A procedure according to claim 3, further comprising fabricating the dental prosthetic based on the model.

5. A procedure according to claim 4,
   wherein the generating of the 3D dental impression image data includes taking one or more scans of an optical camera,
   wherein the generating of the 3D x-ray image data includes taking one or more computer tomography scans by an x-ray system,
   wherein at least one of the registering, the removing, and the generating of the model is performed by a computer-aided design (CAD) system, and
   wherein the fabricating of the dental prosthetic is performed using a computer-assisted manufacturing (CAM) milling system.

6. A procedure according to claim 3,
   wherein the model is a computer model.

7. A procedure according to claim 1,
   wherein the image data corresponding to soft tissue is image data on gingival tissue near a tooth within the tooth restoration site.

8. A system for producing a dental prosthetic, the system comprising:
   a memory storing a program; and
   at least one processor operating under control of the program to register three-dimensional (3D) dental impression image data of a tooth restoration site and 3D x-ray image data of the tooth restoration site, automatically remove image data corresponding to soft tissue in the tooth restoration site from the 3D dental impression image data based on a distinction in the 3D x-ray image data between soft tissue and hard tissue, and demarcate, in the 3D dental impression image data, a preparation margin of a prepared tooth from which soft tissue was removed, in the tooth restoration site.

9. A system for according to claim 8, further comprising:
an optical camera configured to generate the 3D dental impression image data; and
an x-ray system configured to generate the 3D x-ray image data.

10. A system according to claim 9,
wherein the at least one processor further operates under control of the program to generate a model of the dental prosthetic based on the 3D dental impression data in which the image data corresponding to soft tissue in the tooth restoration site has been removed, and
wherein the system further comprises a milling system configured to fabricate a dental prosthetic based on the model of the dental prosthetic.

11. A system according to claim 8,
wherein the image data corresponding to soft tissue is image data on gingival tissue near a tooth within the tooth restoration site.

12. A system according claim 8,
wherein the at least one processor is included in a dental computer-aided design/computer-assisted manufacturing (CAD/CAM) device.

13. A non-transitory computer-readable medium storing sequences of instructions, the sequences of instructions including instructions which, when executed by a computer system, cause the computer system to:
register three-dimensional (3D) dental impression image data of a tooth restoration site and 3D x-ray image data of the tooth restoration site;
automatically remove image data corresponding to soft tissue in the tooth restoration site from the 3D dental impression image data based on a distinction in the 3D x-ray image data between soft tissue and hard tissue; and
demarcate, in the 3D dental impression image data, a preparation margin of a prepared tooth from which soft tissue was removed, in the tooth restoration site.

14. A computer-readable medium according to claim 13,
wherein the instructions, when executed by the computer system, further cause the computer system to:
receive the 3D dental impression image data; and
receive 3D x-ray image data of the tooth restoration site.

15. A computer-readable medium according to claim 14,
wherein the instructions, when executed by the computer system, further cause the computer system to generate a model of a dental prosthetic based on the 3D dental impression image data in which the image data corresponding to soft tissue in the tooth restoration site has been removed.

16. A computer-readable medium according to claim 15,
wherein the instructions, when executed by the computer system, further cause the computer system to fabricate the dental prosthetic based on the model.

17. A computer-readable medium according to claim 13,
wherein the image data corresponding to soft tissue is image data on gingival tissue near a tooth within the tooth restoration site.

18. A procedure for creating a dental prosthetic, the procedure comprising:
registering three-dimensional (3D) dental impression image data of a tooth restoration site and 3D volume image data of the tooth restoration site;
automatically removing image data corresponding to soft tissue in the tooth restoration site from the 3D dental impression image data based on a distinction in the 3D volume image data between soft tissue and hard tissue; and
demarcating, in the 3D dental impression image data, a preparation margin of a prepared tooth from which soft tissue was removed, in the tooth restoration site.

19. A procedure according to claim 18, further comprising generating a model of a dental prosthetic based on the 3D dental impression image data in which the image data corresponding to soft tissue in the tooth restoration site has been removed.

20. A procedure according to claim 18,
wherein the 3D volume image data includes one or more scans generated by one of cone-beam computed tomography, tomosynthesis, ultrasonography, magnetic resonance imaging, and positron emission tomography.

* * * * *